United States Patent [19]
Montastier et al.

[11] Patent Number: 5,869,034
[45] Date of Patent: *Feb. 9, 1999

[54] USE OF SPHINGOLIPIDS IN THE PREPARATION OF A COSMETIC OR DERMOPHARMACEUTICAL COMPOSITION PROTECTING THE SKIN AND HAIR AGAINST THE HARMFUL EFFECTS OF ATMOSPHERIC POLLUTION

[75] Inventors: Christiane Montastier, Maisons-Laffitte; Jacqueline Griat, Ablon, both of France

[73] Assignee: L'Oreal, Paris, France

[*] Notice: The term of this patent shall not extend beyond the expiration date of Pat. No. 5,683,684.

[21] Appl. No.: 871,681

[22] Filed: Jun. 9, 1997

Related U.S. Application Data

[63] Continuation of Ser. No. 122,491, filed as PCT/FR92/0032, Apr. 3, 1992, Pat. No. 5,683,684.

[30] Foreign Application Priority Data

Apr. 3, 1991 [FR] France ................... 91-04053

[51] Int. Cl.⁶ ..................... A61K 7/48
[52] U.S. Cl. ............ 424/78.03; 424/401; 424/43; 424/47; 424/59; 424/70.14; 424/70.122; 424/70.9
[58] Field of Search ................. 424/405, 70.9, 424/70.14, 70.122, 78.03, 40.1, 43, 45, 47, 59

[56] References Cited

U.S. PATENT DOCUMENTS

| | | | |
|---|---|---|---|
| 4,919,920 | 4/1990 | Devos | 424/61 |
| 5,002,761 | 3/1991 | Mueller | 424/70.1 |
| 5,017,368 | 5/1991 | Sugiyama et al. | 424/70 |
| 5,149,860 | 9/1992 | Zysman | 560/160 |
| 5,683,684 | 11/1997 | Montastier et al. | 424/78.03 |

FOREIGN PATENT DOCUMENTS

| | | |
|---|---|---|
| 2652002 | 3/1991 | France . |
| 260008 | 11/1986 | Japan . |
| 260508 | 6/1987 | Japan . |
| 2177092 | 1/1987 | United Kingdom . |
| 8600015 | 1/1986 | WIPO . |
| 8800044 | 1/1988 | WIPO . |

OTHER PUBLICATIONS

West and Todd, Textbook of Biochemistry, pp. 157–158 Jan. 1966.

Patent Abstracts of Japan, vol. II, No. 115 (C–415)(2562) Apr. 1987 re JPA 61–260008.

Patent Abstracts of Japan, vol. II, No. 349 (C–456)(2796) Nov. 1987 re JPA 62–120308.

*Primary Examiner*—Neil S. Levy
*Attorney, Agent, or Firm*—Nixon & Vanderhye P.C.

[57] ABSTRACT

Use of at least one sphingolipid or analogue, optionally in association with a chelating agent, as the active ingredient in the preparation of a cosmetic, sanitary or dermopharmaceutical composition for protecting skin and/or hair against the harmful effects of atmospheric pollution by heavy metals. Application especially in combatting the effects of rapid ageing of the skin and lacklustre appearance of hair caused by atmospheric pollution.

13 Claims, No Drawings

USE OF SPHINGOLIPIDS IN THE PREPARATION OF A COSMETIC OR DERMOPHARMACEUTICAL COMPOSITION PROTECTING THE SKIN AND HAIR AGAINST THE HARMFUL EFFECTS OF ATMOSPHERIC POLLUTION

This is a Continuation of application Ser. No.08/122,491, filed as PCT/FR92/0032 Apr. 3, 1992 now U.S. Pat. No. 5,683,684.

The subject of the invention is the use of sphingolipids or analogous compounds, optionally in combination with a chelating agent, in the preparation of a cosmetic, hygienic or dermopharmaceutical composition protecting the skin and hair against the harmful effects of pollution of the atmosphere by heavy metals.

The invention also relates to the novel cosmetic, hygienic or dermopharmaceutical compositions thus obtained.

Specialists currently consider that one of the causes of cell ageing is the weakening in the abilities to defend against free radicals and the oxidation phenomena which they initiate.

It is known that the toxicity of the gaseous pollutants of the air, such as sulphur dioxide, ozone and nitrogen oxides, is related in particular to their free radical initiator activity which causes cell damage in living creatures; see, for example, H. Mehlhorn et al., Free Rad. Res. Comms., Vol. 3, No. 1, p. 193–197 (1987).

Living cells have various means of defense against free radicals. In particular, certain enzymatic systems (such as superoxide dismutases or SOD and glutathione reductases or GR) destroy free radicals.

Moreover, it is known that heavy metals (lead, cadmium, mercury) are atmospheric pollutants whose emissions have notably increased, especially in the urban or industrial environment.

Besides certain toxic effects which are specific to them, heavy metals have the property of reducing the activity of cell defence means (SOD, GR) against free radicals; see, for example, R. S. Dwivedi, J. Toxicol.-Cut. & Ocular Toxicol. 6(3), 183, 191 (1987).

Thus, heavy metals aggravate the toxic effects of gaseous atmospheric pollutants by reducing the efficiency of the natural defence means, and cause an acceleration in the phenomenon of cell ageing.

This is in particular true for the skin and scalp, which are in direct and permanent contact with the external environment.

The harmful effects of heavy metals are reflected in particular by an accelerated ageing of the skin, with a complexion lacking radiance, and premature formation of wrinkles or furrows, and also by a reduction in the strength and a lacklustre appearance of the hair.

The subject of the present invention is to overcome these effects, harmful from the aesthetic and/or health viewpoint, which result from the pollution of the air by heavy metals.

The subject of the invention is thus the use of at least one sphingolipid or sphingolipid analogue as active ingredient in the preparation of a cosmetic, hygienic or dermopharmaceutical composition intended for protecting the skin and/or hair against the harmful effects of the pollution of the atmosphere by heavy metals.

The sphingolipid used according to the invention can be natural or synthetic. It is known that natural sphingolipids comprise various classes of compounds: ceramides, sphingomyelins, cerebrosides, sulphatides and gangliosides. Among the natural sphingolipids, mention will be made of the ceramides which are known to be the most important constituents of the lipids of the horny layer of the epidermis; cerebrosides, sphingomyelins, sulphatides and gangliosides are present especially in mammalian cell membranes. Commercial ceramides and cerebrosides exist. Natural sphingolipids are extracted especially from plants, animal skins (in particular pig skins), bovine brains, eggs, blood cells, and the like. They can be prepared especially by extraction according to the processes described in Japanese Patent Applications 86/260008 and 87/120308.

The sphingolipids used according to the invention are especially those which correspond to the formula (I)

$$R_1CO-NHCH(CH_2OR_2)-CHOH-R_3 \qquad (I)$$

in which $R_1$ represents an alkyl, alkenyl, hydroxyalkyl or hydroxyalkenyl group having from 9 to 34 carbon atoms, it being possible for the said hydroxyalkyl and hydroxyalkenyl groups to be esterified by an optionally unsaturated fatty acid having from 9 to 34 carbon atoms, $R_2$ represents—H or the residue of a monosaccharide, an osamine, an oligosaccharide or phosphorylcholine, the said monosaccharide or the said oligosaccharide optionally being substituted by one or a number of sulphate groups or sialic acid residues, and $R_3$ represents an optionally unsaturated aliphatic group having from 10 to 25 carbon atoms, it being possible for the said aliphatic group to be substituted in the alpha position by a hydroxyl or an acyloxy group in which the acyl derives from an optionally unsaturated fatty acid having from 9 to 34 carbon atoms. The optionally unsaturated fatty acid is, for example, lineoleic acid. The monosaccharides or saccharide units (generally from 1 to 4) are chosen, for example, from glucose, galactose, sulphogalactose or N-acetylgalactosamine. The preparation of certain synthetic sphingolipids corresponding to the formula (I) has been described in the French patent application of the Applicant filed on 21 Feb. 1991 under No. 91 02091, entitled: "Ceramides, process for their preparation and their applications in cosmetics and in dermopharmacology". These compounds are prepared by acylation of the amine functional group of a sphingosine or of a dihydrosphingosine. Acylation is carried out, for example, with a acid chloride, a mixed anhydride, a paranitrophenol ester, an N-hydroxysuccinimide ester, a dicyclohexylcarbodiimide ester, a lower alkyl ester, or also an azolide such as an imidazolide or a pyrazolide. There may be mentioned, as synthetic sphingolipids, N-oleoyldihydrosphingosine (formula I where $R_1 =C_{17}H_{33}$, $R_2=H$ and $R_3=C_{15}H_{31}$) and N-linoleoyldihydrosphingosine (formula (I) where $R_1=C_{17}H_{31}$, $R_2=H$ and $R_3=C_{15}H_{31}$), it being possible for these compounds to be prepared especially as described in french Patent Application 91 02091, filed on 20 Feb. 1991.

The commercial sphingolipids of natural origin are most often mixtures of various types of sphingo-lipids, additionally being able to contain phospholipids.

In the composition of the invention, the sphingolipid can be combined with at least one phospholipid.

Among the sphingolipid analogues, mention will in particular be made of those which are described in International Patent Application Wo 86/00015, in Patent Application EP 277,641 and in Patent Applications FR 86 09125 and 89 12423.

In the compositions prepared according to the invention, the sphingolipid or sphingolipid analogue is present at a concentration from 0.05 to 2% by weight and in particular from 0.1 to 0.5% by weight.

Another subject of the invention is a process for the preparation of a cosmetic, hygienic or dermopharmaceutical composition intended to protect the skin and/or hair against the harmful effects of pollution of the atmosphere by heavy metals, characterized in that at least one sphingolipid or one sphingolipid analogue, optionally in combination with a chelating agent, is incorporated, in a suitable vehicle.

To prepare the composition of the invention, the sphingolipid or sphingolipid analogue can in particular be dissolved in a suitable vehicle, especially a fatty, alcoholic or aqueous/alcoholic phase. In addition, if desired, the fatty phase is mixed with an aqueous phase or dispersed in the latter.

The composition obtained is, for example, an emulsion, a gelled emulsion, an aqueous/alcoholic or oil/alcoholic lotion, a vesicular dispersion, a two-phase composition, a spray or an aerosol foam.

These compositions are prepared according to conventional methods. They are provided in particular in the milk, cream or two-phase composition form for caring for the skin or hair, or also in the shampoo form. When the compositions obtained according to the invention are provided in the milk or cream form, they are emulsions of water-in-oil type or oil-in-water type, or also aqueous dispersions of lipid spherules consisting of organized molecular layers containing an encapsulated aqueous phase.

When the compositions are two-phase compositions, they consist of a lower aqueous phase and an upper oily phase comprising the sphingolipid. The ratio by weight between the lower phase and the upper phase is, for example, between 30:70 and 60:40.

When the composition obtained according to the invention is provided in the form of a vesicular dispersion, the constituent lipids of the vesicles can be ionic or nonionic lipids or their mixtures.

According to a specific embodiment of the invention, the sphingolipid or sphingolipid analogue is used in combination with a chelating agent, that is to say with an agent capable of forming, with the metal cations, either coordination bonds or ionic bonds. Among the metal cations, mention may be made of lead, mercury and cadmium. Among the chelating agents which form coordination bonds with the metal cations, mention may in particular be made of the phosphonic derivatives, polyiminoacetic or polyaminoacetic acids such as DTPA (diethylenetriaminepentaacetic acid); phytic acid; amides such as N'-[5-[[4-[[5-(acetylhydroxyamino)pentyl]amino]-1,4-dioxobutyl]hydroxyamino]pentyl]-N-(5-aminopentyl)-N-hydroxybutanediamide or deferoxamine, polythiourea and polyethyleneimines.

Among the phosphonic derivatives, mention will in particular be made of: aminotri(methylenephosphonic) acid, (1-hydroxyethylidene) -1, 1-diphosphonic acid, ethylenediaminetetra(methylenephosphonic) acid, hexamethylenediaminetetra(methylenephosphonic) acid and diethylenetriaminepenta(methylenephosphonic) acid, and their salts.

Among the chelating agents which form ionic bonds with the metal cations, mention may be made of the alginates, preferably sodium alginate, and agarose.

In the composition obtained according to the invention, the chelating agent content is generally less than 1% by weight.

The composition can contain, for example, from 0.05 to 1% by weight and in particular from 0.1 to 0.3% by weight of the chelating agent.

The compositions obtained according to the invention are applied to the skin, the scalp and the hair in conventional amounts according to conventional methods.

The following examples illustrate the invention without, however, limiting it.

EXAMPLE 1

Protective cream for the skin

A cream of the following composition by weight was prepared according to conventional methods:
Sorbitan tristearate 0.9
Glyceryl mono-di-tri-palmito-stearate sold under the tradename of "Monoglyceryl-stearate MGSB" by the Company Nikkol 3
Myristyl myristate 5
2-Ethylhexyl palmitate 4
Hydrogenated isoparaffin (6–8 moles of isobutylene) sold under the tradename "Polysynlane" by the Company Nippon Oil Fats 2.5
Sphingolipid 0.25
Phosphonic complexing agent (Dequest 2046) 0.1 Dimethylpolysiloxane sold under the name "Volatile Silicone 7158" by the Company
Union Carbide 5
Cetyl alcohol (90 % $C_{16}$) 2.5
Polyethylene glycol stearate, polyoxyethylenated with 40 mol of ethylene oxide 2
Preserving agent q.s.
Fragrance q.s.
Sterilized demineralized water q.s. for 100

The sphingolipid is that sold under the name Glycocer by Waitaki.

The phosphonic complexing agent Dequest 2046 is the sodium salt of ethylenediaminetetra(methylenephosphonic) acid sold by Monsanto.

Creams were prepared, in an analogous way, containing, in place of Dequest 2046, one of the following chelating agents: DTPA and phytic acid.

EXAMPLE 2

Two- phase composition

A two-phase composition is obtained by adding to a flask 50% of the oily phase (A) and 50% of the aqueous phase (B) containing the following ingredients (parts by weight):
A. Oily phase
Sphingolipid (Glycocer) 0.1
Octyldodecanol 10
Dimethylpolysiloxane sold under the name "Volatile silicone 7158" by the Company
Union Carbide 60
Isopropyl myristate q.s. for 100
B. Aqueous chase
Condensate of ethylene oxide and of propylene oxide sold under the trade name "Synperonic PE/F87" by the Company ICI 0.5
Potassium dihydrogenphosphate 0.1
Anhydrous dipotassium hydrogenphosphate 0.3
Anhydrous sodium chloride 0.9
Propylene glycol 5
Dequest 2046 0.3
Demineralized water q.s. for 100

EXAMPLE 3

Two-phase composition

It is similar to that of Example 2, the sphingolipid Glycocer being replaced by 0.1 g of N-oleoyldihydrosphingosine.

EXAMPLE 4

Study of the protective role with respect to the cytotoxicity induced by heavy metals This test was carried out on fibroblast cultures and on keratinocyte cultures.

The cytotoxicity induced by increasing doses of heavy metal (cadmium, lead, mercury) is determined.

Cell viability is measured by a vital stain, 3(4,5-dimethylthiazol-2-yl)-2,5-diphenyltetrazolium bromide, or MTT, a yellow compound in the oxidized state, which is reduced by the various mitochondrial enzymes of living cells to insoluble purple-blue formazan; see F. Denizot and R. Lang, J. Immunol. Methods, 89, 271–277 (1986).

After addition of the toxic compound being studied, in the soluble salt form (chloride, sulphate or acetate), to the cell culture, the cytotoxicity is evaluated after 24 hours.

To do this, MTT (at a concentration of 5 mg/ml) is added and then lysis of the cells is caused by addition of isopropanol containing 0.04N HCl which dissolves the formazan produced. The amount of formazan (which is formed solely by the living cells) is evaluated by spectrometry at 570 and 630 nm.

Moreover, to estimate the membrane attacks of the cells the intra-and extracellular lactodehydrogenase (LDH) is assayed. In order to assay the extracellular LDH, part of the culture medium is withdrawn and the Boehringer kit (reference 124907) is used.

In order to assay the intracellular LDH, the culture medium is removed and then lysis of the cells is caused using 0.2% Triton 100. The lysate obtained is used to assay the intracellular LDH using the Boehringer kit.

The chelating agent studied was Dequest 2046 sold by Monsanto.

The sphingolipid was Glycocer sold by Waitaki.

Results a) On the fibroblasts:

MTT Test:

The sphingolipid known as Glycocer, used in Examples 1 and 2, has a protective effect with respect to cadmium and mercury at a charge of $5.10^{-4}$ (weight/volume: weight of the commercial product in g/volume (in ml) of the M.E.M. culture medium).

N-Oleoyldihydrosphingosine has a protective effect with respect to cadmium and lead at a charge of $1.10^{-6}$ (weight/volume: weight of the synthetic product in g/volume (in ml) of M.E.M. culture medium).

The chelating agent has a protective effect with respect to cadmium at a charge of $5.10^{-5}$ (vol/vol (volume of the commercial product in ml/volume of the M.E.M. culture medium in ml)).

LDH Test:

The sphingolipid Glycocer has a protective effect with respect to cadmium, lead and mercury at a charge of $5.10^{-4}$ (weight/volume).

The chelating agent has a protective effect with respect to cadmium and lead at a charge of $5.10^{-5}$ (vol/vol)

b) On the keratinocytes:

MTT Test:

The sphingolipid Glycocer has a protective effect with respect to cadmium and mercury, at the charge indicated above.

The chelating agent has a protective effect with respect to cadmium at the charge indicated above.

LDH Test:

At the charges indicated above, the sphingolipid Glycocer has a protective effect with respect to the three heavy metals studied and the chelating agent has a protective effect with respect to cadmium and lead.

We claim:

1. A process to protect skin or hair or both against harmful effects of pollution of the atmosphere by heavy metals, said process comprising applying to the skin, hair or both of a person likely to be exposed to an atmosphere polluted by heavy metals, a cosmetic, hygienic or dermopharmaceutical composition comprising a sphingolipid in an amount effective to protect said skin or hair or both against said harmful effects of said heavy metals.

2. The process of claim 1 wherein said sphingolipid is a natural sphingolipid selected from the group consisting of a ceramide, a cerebroside, a sphingomyelin, sulphatide and a ganglioside.

3. The process of claim 1 wherein said sphingolipid is a synthetic sphingolipid.

4. The process of claim 1 wherein said sphingolipid has formula (I):

$$R_1CO\text{—}NHCH(CH_2OR_2)\text{-}CHOH\text{-}R_3$$

wherein $R_1$ represents alkyl, alkenyl, hydroxyalkyl or hydroxyalkenyl, having 9 to 34 carbon atoms, $R_2$ represents hydrogen, a monosaccharide, an osamine, an oligosaccharide or phosphorylcholine and $R_3$ represents an aliphatic group having 10 to 25 carbon atoms.

5. The process of claim 4 where, in $R_1$, said hydroxyalkyl or hydroxyalkenyl is esterified by an unsaturated fatty acid having 9 to 34 carbon atoms.

6. The process of claim 4 where, in $R_2$, said monosaccharide or oligosaccharide is substituted by a sulphate group or a sialic acid.

7. The process of Claim 4 wherein $R_3$ is an unsaturated aliphatic group.

8. The process of claim 4 where, in $R_3$, said aliphatic group is substituted in alpha position by hydroxyl or acyloxy wherein the acyl moiety is derived from a fatty acid having 9 to 34 carbon atoms.

9. The process of claim 1 wherein said sphingolipid is combined with a phospholipid other than a sphingolipid.

10. The process of claim 1 wherein said sphingolipid is present in said composition in an amount ranging from 0.05 to 2 percent by weight based on the total weight of said composition.

11. The process of claim 1 wherein said sphingolipid is present in said composition in an amount ranging from 0.1 to 0.5 percent by weight based on the total weight of said composition.

12. The process of claim 1 wherein said sphingolipid is dissolved in a fatty, alcoholic, oil/alcoholic or aqueous/alcoholic phase.

13. The process of claim 1 wherein said composition is an emulsion, a gelled emulsion, an aqueous/alcoholic lotion, an oil/alcoholic lotion, a vesicular dispersion, a two-phase composition, a spray or an aerosol foam.

* * * * *